United States Patent [19]
Fridinger

[11] 3,948,987
[45] Apr. 6, 1976

[54] SUBSTITUTED METHANESULFONANILIDES

[75] Inventor: Tomas L. Fridinger, Woodbury, Minn.

[73] Assignee: Minnesota Mining and Manufacturing Company, St. Paul, Minn.

[22] Filed: Apr. 19, 1974

[21] Appl. No.: 462,546

[52] U.S. Cl. ............ 260/556 F; 71/103; 260/397.6; 260/556 A; 260/578; 260/609 E; 260/556 S
[51] Int. Cl.² ................ C07C 143/72; C07C 143/84
[58] Field of Search .......... 260/397.6, 556 F, 556 A

[56] References Cited
UNITED STATES PATENTS

| | | | |
|---|---|---|---|
| 3,642,817 | 2/1971 | Harrington et al. | 260/556 F |
| 3,708,491 | 1/1973 | Harrington et al. | 260/556 F |

*Primary Examiner*—Arthur P. Demers
*Attorney, Agent, or Firm*—Alexander, Sell, Steldt & DeLaHunt

[57] ABSTRACT

2-Trifluoromethylmethanesulfonanilides substituted in the para (four) position by phenylthio, phenylsulfinyl or phenylsulfonyl groups and agriculturally acceptable salts thereof and compositions containing these compounds are useful herbicides.

5 Claims, No Drawings

SUBSTITUTED METHANESULFONANILIDES

BACKGROUND OF THE INVENTION

This invention relates to the compounds 4-phenylthio-2-trifluoromethylmethanesulfonanilide, 4-phenylsulfinyl-2-trifluoromethylmethanesulfonanilide and 4-phenylsulfonyl-2-trifluoromethylmethanesulfonanilide and agriculturally acceptable salts thereof. The invention also relates to herbicidal compositions containing said compounds and the use thereof to control the growth of higher plants. Methods for the preparation of the compounds are also included.

The prior art, for example, British Pat. Nos. 738,758; 854,956 and 856,452 and French Pat. No. 1,188,591 describes haloalkylsulfonamido-diphenylthioethers, diphenylsulfoxides and diphenylsulfones, some of which are substituted by trifluorormethyl groups on the phenyl rings. However, no alkylsulfonamidodiphenylthioethers, diphenylsulfoxides or diphenylsulfones are reported, nor is herbicidal activity anywhere mentioned.

Perfluoroalkylsulfonanilides substituted by phenylthio, phenylsulfinyl, and phenylsulfonyl groups are known, see for example South African Pat. No. 7,105,582. These compounds are not reported to be substituted by trifluoromethyl groups. Other publications, for example Trepka, et al., *J. of Ag. and Food Chem.*, p. 1176 (1970) have taught that " . . . herbicidal activity was greatest with the more highly fluorinated . . . " alkylsulfonamido groups of sulfonanilides.

It was therefore very unexpected to find that the alkylsulfonanilides of the present invention showed particularly high and useful activity as herbicides.

DETAILED DESCRIPTION OF THE INVENTION

This invention relates to compounds of the formula

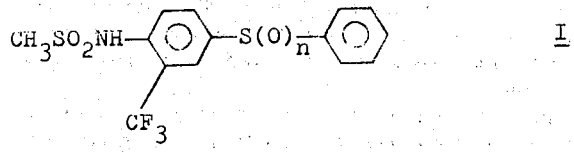

I wherein $n$ is zero, one or two and agriculturally acceptable salts thereof.

The invention also relates to compositions for killing and regulating the growth of higher plants consisting essentially of a compound of the invention dispersed in an extending medium.

The invention also relates to the use of the compounds of the invention to regulate and control the growth of higher plants, and to kill higher plants.

The invention also relates to processes for the preparation of the compounds of the invention.

The acid-form compounds of the invention are acidic, i.e. the amido hydrogen is acidic. Consequently, they form salts, e.g. compounds of Formula I wherein R is an agriculturally acceptable cation. These are generally metal, ammonium, and organic amine salts and can be prepared by treating the acid form with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by cation exchange reactions (by reacting a salt of the invention with an organic or inorganic salt in a cation exchange reaction). The organic amine salts include the salts of aliphatic (e.g. alkyl), aromatic and heterocyclic amines, as well as those having a mixture of these types of structures. The amines useful in preparing the salts of the invention can be primary, secondary, or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form compound with the appropriate organic base or ammonium hydroxide. Any of the salts of the types set out above are agriculturally acceptable, the one chosen depending upon the particular use and upon the economics of the situation.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetone, etc. The resulting solution is then treated to remove the solvent, for example, by evaporation under reduced pressure. Since some of the salts are water soluble, they are often used in the form of aqueous solutions.

The compounds of the invention are prepared according to the reaction sequences outlined below:

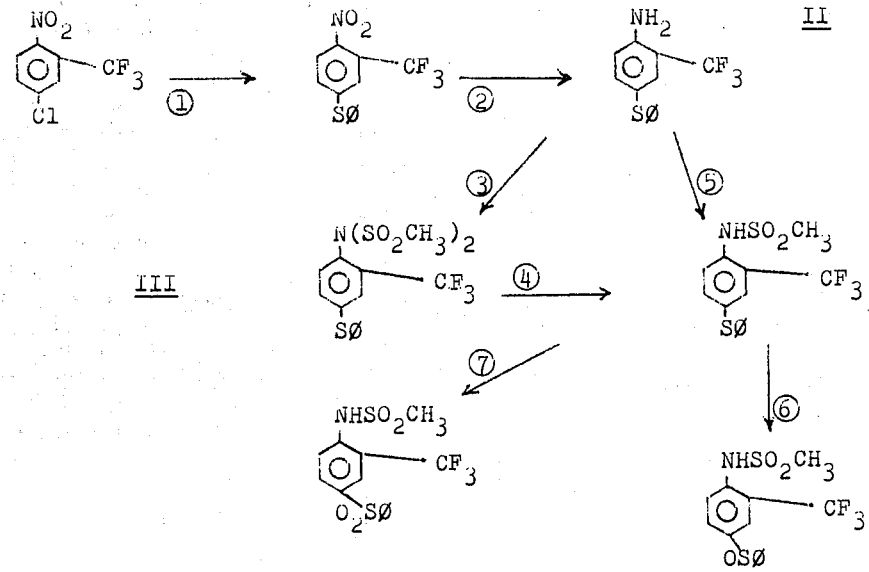

The reaction of step 1 is carried out by heating equimolar amounts of 5-chloro-2-nitrobenzotrifluoride and benzenethiol in a suitable inert solvent in the presence of an equimolar amount of base. The inert solvent is one in which the reactants are soluble such as a lower alkanol (e.g. ethanol or methanol), dimethyl sulfoxide and N,N-dimethyl formamide. The base is an organic or inorganic base. Suitable organic bases are tertiary amines such as N,N-dimethylaniline, triethylamine, pyridine, alkoxides such as sodium ethoxide, and the like. Suitable inorganic bases are alkali metal hydroxides, such as sodium and potassium hydroxides, calcium hydride, sodium carbonate, sodium bicarbonate and the like. The product is isolated by conventional methods.

The reaction of step 2 is a reduction of the nitro group of the novel intermediate 2-nitro-5-phenylthiobenzotrifluoride. Chemical or catalytic methods well known to the art are successful. Raney nickel is one suitable catalyst for the reduction. The product is isolated by conventional methods.

The reaction of step 3 is the methanesulfonylation of the novel intermediate 4-phenylthio-2-trifluoromethylaniline (II) with two or more moles of methanesulfonyl chloride in the presence of a base. If one to two moles of methanesulfonyl chloride are used a mixture of mono- and dimethanesulfonylated product is obtained which may be used in step 4. If two or more moles of methanesulfonyl chloride are reacted, the product obtained is the novel intermediate (III). Suitable bases for the reaction of step 3 are organic or inorganic bases such as pyridine, triethylamine, N,N-dimethylaniline and substituted pyridines, and the like. Liquid bases in excess can be used to eliminate the need for a solvent. Stronger bases promote the formation of intermediate (III) over the product of steps 4 and 5.

Step 4 is partial hydrolysis of the novel intermediate (III) to the final product. This is a surprisingly high yield reaction. Basic hydrolysis using a strong base such as potassium hydroxide in ethanol is used.

Step 5 is mono-methanesulfonylation of intermediate (II). This reaction requires the use of equimolar amounts of intermediate (II) and methanesulfonyl chloride and selection of a base weaker than pyridine, such as 3-bromopyridine, in order to provide good yields of the desired product.

Steps 6 and 7 are both carried out using known oxidation techniques, such as hydrogen peroxide in acetic acid, sodium metaperiodate, and the like. Step 6 requires one mole of peroxide per mole of reactant, while step 7 uses two moles (or a slight excess) of peroxide per mole of reactant.

The herbicidal activity of the compounds of the invention has been determined using screening tests against greenhouse plantings. Both pre- and post-emergence activity are determined in a direct screen against selected weed species. The following weeds are examples of weeds which are used for these tests.

Grasses:
  Giant foxtail (*Setaria faberii*)
  Barnyard grass (*Echinochloa crusgalli*)
  Crabgrass (*Digitaria ischaemum*)
  Quackgrass (*Agopyron repens*)
Broadleaves:
  Pigweed (*Amarantnus retroflexus*)
  Purslane (*Portulaca oleracea*)
  Wild Mustard (*Brassica kaber*)
  Wild Morning Glory (*Convolvulus arvensis*)

The test chemicals are dissolved in a small amount of acetone or other suitable solvent and then diluted with water to give a concentration of 2000 ppm. From this concentration aliquots are diluted to give a final concentration of 500 ppm. To assess pre-emergence activity, eighty ml. of this solution are added to a 6-inch pot containing the weed seeds to give a concentration equal to 5 lb./acre. All subsequent waterings are made from the bottom. Two pots are used per treatment. Data are taken two to three weeks after treatment and recorded as percent pre-emergence kill for each species compared to the untreated controls.

To assess post-emergence activity, the same weed mixtures are allowed to grow from two to three weeks until the grasses are approximately 1 to 3 inches and the broadleaves 1½ inches tall. They are sprayed for approximately 10 seconds or until good wetting of the leaf surfaces occurs with a 2000 ppm solution as described above.

Data are taken two to three weeks after treatment and recorded as percent kill for each species compared to the untreated controls.

The compounds of this invention are broadly active as herbicides. The mechanism(s) by which this herbicidal activity is effected is not presently known. However, many of the compounds of this invention also show various types of plant growth modifying activity. Plant growth modification as defined herein consists of all deviations from natural development, for example defoliation, stimulation, stunting, retardation, dessication, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants.

The compounds of the invention have been found to be particularly effective in controlling nutsedge (for example *Cyperus esculentus* and *Cyperus rotundus*) species. Nutsedge is considered one of the major weed pests of the world. This weed is resistant to most herbicides, and has become an increasingly severe problem. It is a particularly severe problem when other weed species are controlled by herbicides and nutsedge becomes the dominant weed. It was unexpected to find outstanding control of nutsedge in the compounds of the invention.

For application to plants, the compounds can be finely divided and suspended in any of the usual aqueous media. In addition, spreading agents, wetting agents, sticking agents or other adjuvants can be added as desired. Dry powders, as such or diluted with inert materials such as diatomaceous earth, can likewise be used as dusts for this purpose.

Wettable powder formulations suitable for applying the compounds comprise a clay base, 1–2 percent of a wetting agent (such as Nekal BX-78, an alkyl naphthalene sulfonate available from the General Aniline and Film Corporation), 3–5 percent of a dispersing agent (such as Marasperse N-22, a lignosulfonate product available from the American Can Company) and the active ingredient, the percentages being based on the weight of the entire formulation. A particularly suitable formulation is a 50 percent wettable powder containing (on a weight basis) 50 percent of the active ingredient, 1.5 percent of Nekal BX-78, 4.0 percent of Marasperse N-22 and the remainder, 44.5 percent, of the clay.

The preparations are coated on the plants or the ground is covered when pre-emergence control is desired. Application is made with the usual sprayers, dust guns and the like. Application rates are at 0.5 to 20 lbs./acre in general, but may be increased or reduced according to individual circumstances of use.

When it is desired to maximize the weed spectrum to be controlled, or to better control a weed not well controlled by specific compounds of the invention, they may be used in combination with other herbicides such as phenoxy herbicides, e.g. 2,4-D; 2,4,5-T, silvex and the like, carbamate herbicides, thiocarbamate and dithiocarbamate herbicides, substituted urea herbicides, e.g. diuron, monuron, and the like, triazine herbicides, e.g. simazine and atrazine, chloroacetamide and chlorinated aliphatic acid herbicides, chlorinated benzoic and phenylacetic acid herbicides such as chloramben and other herbicides such as trifluralin, paraquat, nitralin and the like. Furthermore, herbicidal compositions containing compounds of the invention may contain, in addition, nematicides, fungicides, insecticides, fertilizers, trace metals, soil conditioners, plant growth regulators and the like.

Since certain compounds of the invention are particularly active against nutsedge, it is particularly advantageous to combine them with other known nerbicides to broaden the weed spectrum controlled by herbicidal compositions of this invention. Such herbicidal combinations are clearly envisioned in this invention.

The following examples are given for the purpose of further illustrating the procedures of the present invention, but are not intended, in any way, to be limiting on the scope of the invention.

EXAMPLE 1

2-Nitro-5-phenylthiobenzotrifluoride

A solution of 2-nitro-5-chlorobenzotrifluoride (33.8 g, 0.15 mole), benzenethiol (16.6 g, 0.15 mole) and ethanol (150 ml) is heated to its reflux temperature under nitrogen. To this solution is slowly added a solution of sodium hydroxide (6 g, 0.15 mole) and water (7 ml) at such a rate that refluxing continues with no external heating. the solution is then heated at its reflux temperature for an additional two hours, filtered hot and the filtrate cooled. The resulting precipitate is collected by filtration and recrystallized from hexane to afford a yellow solid, m.p. 65°–67° C.

Analysis: Calculated for $C_{13}H_8F_3NO_2S$: %C, 52.2, %H, 2.7, %N, 4.7. Found: %C, 52.2, %H, 2.6, %N, 4.7.

EXAMPLE 2

4-Phenylthio-2-trifluoromethylaniline

2-Nitro-5-phenylthiobenzotrifluoride (25.6 g, 0.86 mole) in ethanol (500 ml) is reduced over Raney nickel at about 45 psi of hydrogen gas. After hydrogen uptake is complete the mixture is deactivated with elemental sulfur, filtered, and the filtrate evaporated under reduced pressure to afford product as an oil. The infrared spectrum shows an absorption at 2.9μ (strong NH band). The product crystallizes on standing to give a solid, m.p. 63°–66.5° C.

EXAMPLE 3

4-Phenylthio-2-trifluoromethylmethanesulfonanilide

To a cold (0°–15° C.), stirred solution of 4-phenylthio-2-trifluoromethylaniline (715.7 g, 2.66 mole) in pyridine (1780 ml) is added over about 3 hours methanesulfonyl chloride (762 g, 6.65 mole). The solution is stirred at room temperature for 2 days, poured into 3 liters of ice and 500 ml concentrated hydrochloric acid, and the resulting solid collected by filtration, washed with water and dried. This product, m.p. 139°–143° C., is crude N-methylsulfonyl-4-phenylthio-2-trifluoromethylmethanesulfonanilide.

N-Methylsulfonyl-4-phenylthio-2-trifluoromethanesulfonanilide (1129 g, 2.66 mole), is added to a solution of 85% potassium hydroxide (528 g, 8.0 mole) and ethanol (4 l.) and the mixture stirred overnight at room temperature. The tan solid is collected by filtration, dissolved in hot water and the resulting solution acidified with dilute hydrochloric acid. The precipitated solid is collected by filtration, washed with water, partially dried in air, and further dried by dissolving in methylene chloride, treating with magnesium sulfate and precipitating with hexane. The product is an off-white solid, m.p. 78°–81° C.

Analysis: Calculated for $C_{14}H_{12}F_3NO_2S_2$: %C, 48.4, %H, 3.5, %N, 4.0. Found: %C, 48.5, %H, 3.5, %N, 4.0.

EXAMPLE 4

4-Phenylsulfinyl-2-trifluoromethylmethanesulfonanilide

To a stirred solution of 4-phenylthio-2-trifluoromethylmethanesulfonanilide (200 g, 0.58 mole) in glacial acetic acid (700 ml) is added 30% hydrogen peroxide (65.3 g, 0.58 mole). The solution is stirred at room temperature (slight exotherm to about 40° C.) overnight, heated to its reflux temperature and about 400 ml water is then added to the hot solution. The solution is cooled, the precipitate collected by filtration, washed with water and dried to give a white solid, m.p. 156°–159° C.

Analysis: Calculated for $C_{14}H_{12}F_3NO_3S_2$: %C, 46.3, %H, 3.3, %N, 3.9. Found: %C, 46.4, %H, 3.5, %N, 3.9.

EXAMPLE 5

4-Phenylsulfonyl-2-trifluoromethylmethanesulfonanilide

A solution of 4-phenylthio-2-trifluoromethylmethanesulfonanilide (200 g, 0.58 mole) in glacial acetic acid (700 ml) is heated to its reflux temperature and 30% hydrogen peroxide (196 g, 1.73 mole) is added dropwise at such a rate that refluxing is maintained with little or no external heating. The solution is heated at reflux an additional 2½ hours, water (150 ml) added, and the mixture cooled. The precipitate is collected by filtration, washed with water and dried to give a white solid, m.p. 176°–178° C.

Analysis: Calculated for $C_{14}H_{12}F_3NO_4S_2$: %C, 44.3, %H, 3.2, %N, 3.7. Found: %C, 44.5, %H, 3.2, %N, 3.7.

EXAMPLE 6

N-Methylsulfonyl-4-phenylthio-2-trifluoromethylmethanesulfonanilide

To a cold (0°–15° C.), stirred solution of 4-phenylthio-2-trifluoromethylaniline (16.1 g, 0.06 mole) in pyridine (14.2 g) is added dropwise methanesulfonyl chloride (7.6 g, 0.066 mole). The solution is stirred at room temperature for about 2 days, poured into ice water (200 ml) and concentrated hydrochloric acid (80 ml), and the resulting solid collected by filtration, washed with water and dried. Two recrystallizations from a mixture of hexane and methylene chloride affords an off-white solid, m.p. 145°–148° C.

Analysis: Calculated for $C_{15}H_{14}F_3NO_4S_3$: %C, 42.3, %H, 3.3, %N, 3.3. Found: %C, 42.5, %H, 3.3, %N, 3.3.

EXAMPLE 7

4-Phenylthio-2-trifluoromethylmethanesulfonanilide

To a cold (0° C.) stirred solution of 4-phenylthio-2-trifluoromethylaniline (2.7 g, 10 mmole), dimethylformamide (5 ml) and 3-bromopyridine (1.25 g) is added methanesulfonyl chloride (1.14 g, 10 mmole). The solution is stirred at room temperature for 24 hours, washed with dilute hydrochloric acid and water, dried over magnesium sulfate, and the solvent evaporated under reduced pressure to afford a solid product, whose thin layer chromatography $R_f$ value in ethyl acetate-hexane matches that observed for pure, authentic 4-phenylthio-2-trifluoromethylmethanesulfonanilide of Example 3.

What is claimed is:

1. A compound of the formula

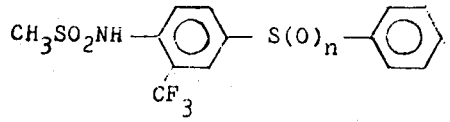

wherein $n$ is zero, one or two and agriculturally acceptable salts thereof.

2. The compound 4-phenylthio-2-trifluoromethylmethanesulfonanilide according to claim 1.

3. The compound 4-phenylsulfinyl-2-trifluoromethylmethanesulfonanilide according to claim 1.

4. The compound 4-phenylsulfonyl-2-trifluoromethylmethanesulfonanilide according to claim 1.

5. The compound N-methylsulfonyl-4-phenylthio-2-trifluoromethylmethanesulfonanilide.

* * * * *